United States Patent [19]

Kontos

[11] 4,267,846
[45] May 19, 1981

[54] CONTROLLED VOLUME BLOOD SAMPLING SYRINGE

[75] Inventor: Stavros B. Kontos, Oakland, N.J.
[73] Assignee: Critikon, Inc., Tampa, Fla.
[21] Appl. No.: 7,135
[22] Filed: Jan. 29, 1979
[51] Int. Cl.³ .............................................. A61B 5/14
[52] U.S. Cl. .................................. 128/765; 128/766; 128/218 C
[58] Field of Search ........ 128/765, 766, 763, 218 PA, 128/218 C

[56] References Cited

U.S. PATENT DOCUMENTS

| 772,114 | 10/1904 | Pappenheim | 128/218 PA |
| 3,237,660 | 3/1966 | Hill | 128/218 C |
| 3,281,023 | 10/1966 | Bruck et al. | 128/218 C X |
| 3,770,026 | 11/1973 | Isenberg | 128/218 C X |
| 3,815,785 | 6/1974 | Gilmont | 128/218 C X |
| 3,831,602 | 8/1974 | Broadwin | 128/218 PA |
| 3,835,835 | 9/1974 | Thompson et al. | 128/765 X |
| 4,073,321 | 2/1978 | Moskowitz | 128/218 C X |
| 4,178,941 | 12/1979 | Raitto | 128/763 |

FOREIGN PATENT DOCUMENTS

| 882743 | 3/1943 | France | 128/218 C |
| 53020 | 9/1944 | France | 128/218 C |
| 786931 | 11/1957 | United Kingdom | 128/218 C |

Primary Examiner—Kyle L. Howell
Attorney, Agent, or Firm—Donal B. Tobin

[57] ABSTRACT

A syringe useful for taking samples of blood includes a barrel with a hollow needle at one end and a plunger positioned inside the barrel for regulating the amount of fluid inside the barrel. In order to control the volume inside the barrel which receives and contains the blood sample, a control element is associated with the plunger and the barrel to control the distance which the plunger can move in both inward and outward directions.

1 Claim, 5 Drawing Figures

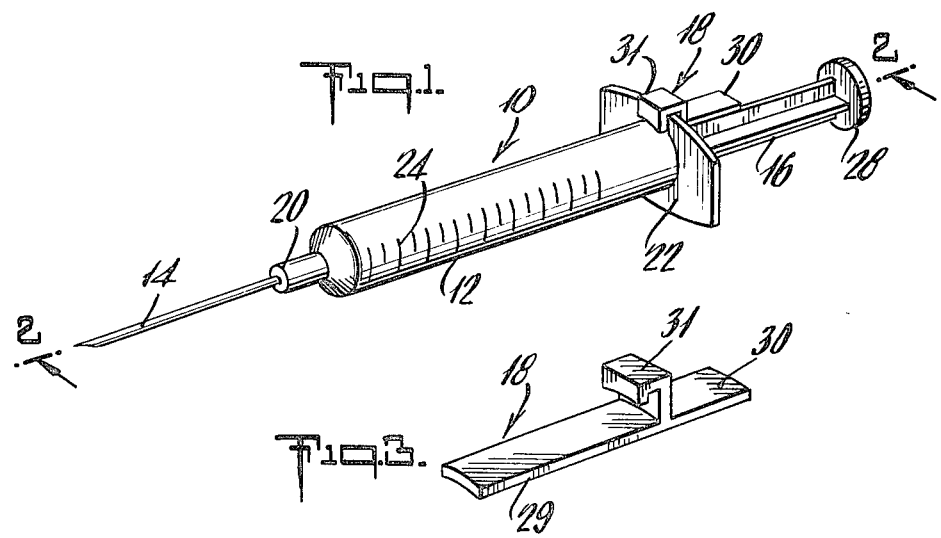
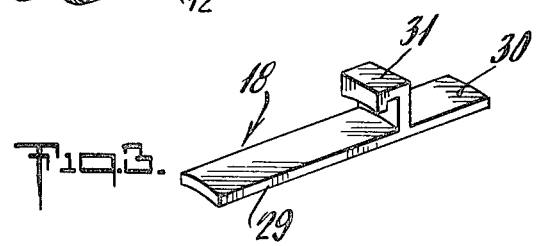
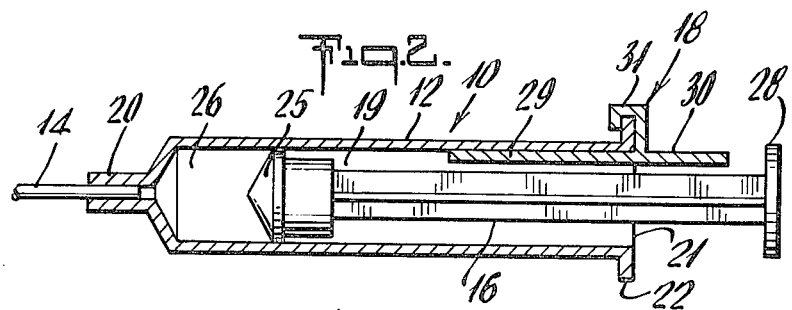
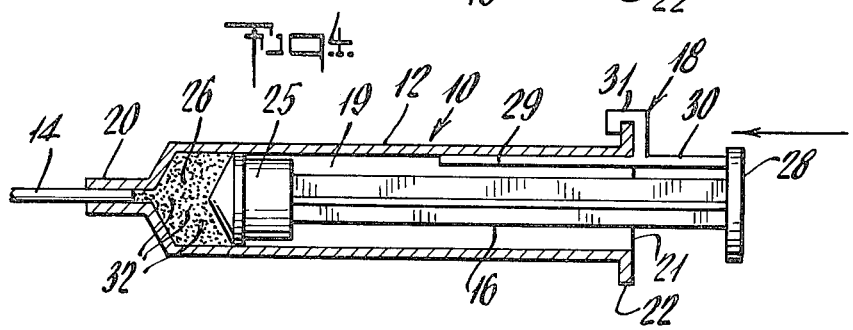
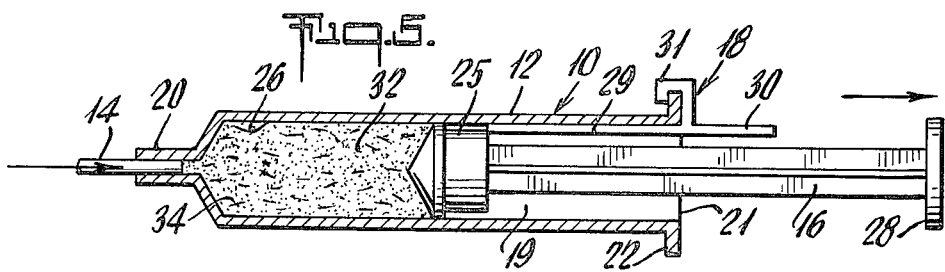

CONTROLLED VOLUME BLOOD SAMPLING SYRINGE

BACKGROUND OF THE INVENTION

The present invention relates to a syringe for injecting fluids into or withdrawing them from a patient, and more particularly, concerns a syringe useful for taking samples of blood from the patient.

In the procedure of withdrawing blood from a patient for sampling purposes, the blood is collected in a syringe following which it is analyzed. The standard syringe includes a barrel into which a plunger is slidably fit and a needle projecting from the barrel. Following venipuncture of the patient, the blood travels through the hollow needle upon rearward withdrawal of the plunger. When sufficient volume of blood has been collected, the withdrawal of the plunger is stopped and the syringe is removed from the patient. In using this procedure, it has been found that the clotting time of blood is significantly reduced by incorporating a small amount of anticoagulant into the blood sample. Some problems arise, however, with the inclusion of this anticoagulant in the blood sample.

Specifically, the use of anticoagulants, such as heparin, may affect various characteristics of the blood sample such as the partial pressure of carbon dioxide and the pH. Since it is desirable to pre-package the syringe with the anticoagulant in the barrel previous to the collection in the blood sample, it is imperative to control the volume of the anticoagulant in order to minimize or eliminate its effect on the blood characteristics. Accordingly, the volume inside the barrel requires an effective measure of control so that the amounts of anticoagulant may be regulated and, in addition, the amount of collected blood can be regulated so that the ratio of collected blood to anticoagulant can be a known factor.

Although various means have been known in the art of syringes for controlling plunger movement relative to the barrel, such as the control features found in U.S. Pat. Nos. 2,607,343 and 2,216,354, the art has been deficient in providing a suitable syringe to control both the inward and the outward movement of the plunger to effectively control the volume inside the barrel. Therefore, it is toward the solution of this deficiency that the present invention is directed.

SUMMARY OF THE INVENTION

A syringe useful for taking samples of blood comprises a barrel having a bore therethrough. A distal end of the barrel is adapted to be connected to a hollow needle so that the lumen of the needle and the bore are in fluid communication. At the proximal end of the barrel, the bore is open. A plunger is slidably positioned in the bore and it includes a piston at its forward end providing a fluid-tight seal against the wall of the barrel. A rearward end of the plunger extends outwardly beyond the proximal end of the barrel. Means is associated with the plunger and the barrel to control the distance which the plunger can move in both inward and outward direction to thereby control the volume inside the barrel.

In a preferred embodiment of the present invention, the control means is a one-piece stop element connected to the barrel. This stop element has a first arm extending into the bore positioned to engage the plunger upon its outward movement to thereby limit the outward travel of the plunger. A second arm of the stop element extends rearwardly beyond the proximal end of the barrel and is positioned to engage the plunger upon its inward movement to thereby limit the inward travel of the plunger.

From the structural standpoint, the syringe of the present invention is notably different from prior art structures in that it provides the control means for regulating both the inward movement of the plunger relative to the barrel so that the volume inside the barrel can be effectively controlled. As a result of the structural configuration of the present invention, a number of advantages are offered. Particularly, an anticoagulant may be included as a pre-packaged element in the barrel of the syringe so that the volume of the anticoagulant is controlled and measured by the final inward stroke and position of the plunger. In addition, the amount of blood which is collected is controlled by the outward travel of the plunger since the maximum volume inside the barrel is regulated by the travel control features of this present invention. Furthermore, in addition to controlling volume inside the barrel, the stop element of the present invention also serves to prevent accidental removal of the plunger during the blood collecting procedure. The syringe of the present invention is inexpensively fabricated and its volume control features conveniently and positively produce the desired control effect.

BRIEF DESCRIPTION OF THE DRAWINGS

FIG. 1 is a perspective view of the preferred syringe of the present invention;

FIG. 2 is a cross-sectional view taken along line 2—2 of FIG. 1;

FIG. 3 is an enlarged perspective view illustrating the preferred embodiment of the stop element for controlling the inward and outward travel of the plunger;

FIG. 4 is a cross-sectional view illustrating the the control of the inward movement of the plunger; and FIG. 5 is a cross-sectional view illustrating the control of the outward movement of the plunger.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is shown the preferred syringe 10 of the present invention. This syringe is composed generally of a barrel 12, a hollow needle 14, a plunger 16 and a stop element 18 for controlling the inward and outward movement of plunger 16. These general components are illustrated in greater detail in FIGS. 2 and 3.

Barrel 12 is preferably a long cylindrical tube-shaped element in which its interior space is a bore 19 extending completely through the barrel. At the distal end 20 of the barrel, it is fabricated and shaped to receive hollow needle 14 so that the needle is effectively sealed in a fluid-tight connection to the distal end of the barrel. This connection assures that the lumen of the hollow needle will be in a fluid communication with the bore of the barrel. Bore 19 is open at the proximal end 21 of the barrel; at this proximal end a flange 22 extends substantially perpendicular to the longitudinal axis of the barrel and provides a convenient finger grip for the user of the syringe during its operation.

Inasmuch as the barrel serves as the container for the collection of the blood sample, it is preferably made of a transparent plastic material so that the operator can visualize the blood collecting procedure. It is also desirable for the inside wall of the barrel surrounding the bore to be smooth surfaced so as to facilitate the sliding of the plunger inside the bore. For convenience during use the barrel is preferably marked with gradation markings 24 as more clearly seen in FIG. 1.

Plunger 16 is an elongate member which is smaller in cross-section than the diameter of the bore of the barrel, and is somewhat longer in length that the length of the barrel. At the forward end of plunger 16 is a piston 25. Plunger 16 and piston 25 are slidably positioned in the bore of the barrel with piston 25 directed toward distal end 20 of the barrel. The piston is of sufficient size and shape to snugly fit in the bore of the barrel while providing a fluid-tight seal against the wall of the barrel. Thus, any fluids which are contained in the cavity space 26 of the bore will be effectively contained therein without escaping out of the barrel due to the seal between the piston and the wall of the barrel. Since plunger 16 is somewhat longer than the barrel, its rearward end extends outwardly beyond proximal end 21 of the barrel and terminates in a button-like disc 28, which serves as a convenient surface against which the thumb of the user presses the plunger inwardly. The plunger is preferably made of plastic material except that piston 25 preferably has a rubber or other elastomer peripheral surface in order to provide an effective fluid-tight seal against the wall of the barrel.

As seen more clearly in FIGS. 2 and 3, stop element 18 is provided in order to control the inward and outward movement of plunger 16. Although various control devices and stop means may be employed for this purpose, the preferable stop element 18 of the present invention is a one-piece item which is structured to control both inward and outward movement of the plunger relative to the barrel. Stop element 18 includes a first arm 29 and a second arm 30, each of the respective arms extending in opposite directions from a hook 31 which rises substantially perpendicular to the plane of the respective arm. Although it is not essential, first arm 29 is longer than second arm 30 inasmuch as the first arm is intended to be inserted into the elongate barrel. As seen more clearly in FIG. 2, hook 31 is sized and shaped to snap fit over flange 22 at the proximal end of the barrel. At the same time, first arm 29 is inserted into the bore and extends along the space between the inside wall of barrel 12 and plunger 16; inasmuch as both first arm 29 and second arm 30 are in the same plane, second arm 30 extends rearwardly beyond the proximal end of the barrel.

FIGS. 4 and 5 illustrate the function of the stop element in controlling the volume inside the syringe barrel. Turning to FIG. 4 in particular, syringe 10 is illustrated as it may appear prior to venipuncture with a small amount of anticoagulant 32, such as heparin or the like, contained in cavity 26 toward the distal end of the barrel. This anticoagulant is pre-packaged in the syringe and remains in cavity 26 until the syringe is ready for use. Hollow needle 14 is usually adequately capped in order to prevent the anticoagulatn from escaping through the needle before use. Just prior to venipuncture, the user of the syringe removes the cap from the needle and moves plunger 16 inwardly by pressing against disc 28 until the disc abuts against the edge of second arm 30. This inward movement will expel any excess anticoagulant in cavity 26 so that a controlled amount now remains. Second arm 30 effectively prevents the plunger from travelling inward any further; preferably, second arm 30 extends rearwardly and a sufficient distance to prevent piston 25 at the forward end of the plunger from seating against the distal end of the barrel thereby leaving a controlled minimum volume inside the barrel. Thus, any controlled amount of anticoagulant in this space can never be inadvertently expelled.

In FIG. 5 the opposite, outward movement of plunger 16 is illustrated. In this illustration venipuncture has been effected by needle 14; the user then withdraws plunger 16 outwardly by grasping disc 28 and pulling the same in the outward direction. This movement increases the volume in cavity 26 so that blood 34 may be collected in the cavity at the distal end of the barrel. Since the ratio of collected blood to anticoagulant is somewhat critical in the analysis of the blood sample, the volume is controlled by limiting the outward travel of plunger 16. This is accomplished when the forward end of the plunger, or in the embodiment being described, piston 25, strikes the edge of first arm 29. This engagement prevents further outward movement of the plunger, and not only effectively controls the volume of the cavity inside the barrel, but also serves to prevent accidental removal of the plunger from the barrel.

Accordingly, it can be seen that the present invention provides a syringe in which the volume inside the barrel can be effectively controlled due to the regulation of the inward and outward movement of the plunger relative to the barrel. Moreover, the controlling device for both inward and outward movement is a convenient one-piece attachment in its preferable embodiment and serves to provide the control of both inward and outward directions of the plunger.

I claim:

1. A syringe useful for taking samples of blood comprising:

A barrel having a bore therethrough, a distal end of said barrel adapted to be connected to a hollow needle so that the lumen of the needle and the bore are in fluid communication, the bore at the proximal end of the barrel being open;

a flange extending from said barrel about said proximal end thereof, substantially perpendicularly to the longitudinal axis of said barrel;

a plunger slidably positioned in said bore having a piston at its forward end providing a fluid-tight seal against the wall of the barrel, said plunger having a rearward portion extending outwardly beyond the proximal end of said barrel;

a one piece stop element including:

a first arm extending into said bore and having a free end positioned to engage said piston upon its outward movement to thereby limit the outward travel of said plunger;

said first arm having a first surface confronting the inside surface of said barrel and contoured conformingly with the shape of said barrel;

a second arm extending rearwardly beyond the proximal end of said barrel and having a free end positioned to engage the plunger upon its inward movement to thereby limit the inward travel of said plunger;

said first and second arms aligned in a generally co-planar relationship;

a hook having a flexible upstanding portion extending substantially perpendicularly from the plane of said first and second arms between the free ends of said first and second arms;

said hook including an L-shaped portion integrally disposed on and extending from the upper extent of said upstanding portion in a direction of generally parallel to said first and second arms so as to provide a hook adapted to fit over said barrel flange to thereby hold said stop element in position;

whereby said stop element maintains a desired maximum volume of blood that may be collected in the syringe by limiting the rearward travel of said plunger and maintains a desired minimum volume of blood that may be collected in the syringe by limiting the forward travel of said plunger;

said stop element adapted to permit the maximum and minimum volume of said syringe to be maintained for repeated use without adjustment.

* * * * *